United States Patent [19]

Mitchell et al.

[11] 4,086,261
[45] Apr. 25, 1978

[54] METHANATION OVER SYNTHETIC AMORPHOUS SILICAS

[75] Inventors: Thomas Owen Mitchell, Trenton; Darrell Duayne Whitehurst, Titusville, both of N.J.

[73] Assignee: Mobil Oil Corporation, New York, N.Y.

[21] Appl. No.: 738,789

[22] Filed: Nov. 4, 1976

Related U.S. Application Data

[60] Continuation-in-part of Ser. No. 638,405, Dec. 8, 1975, Pat. No. 4,003,825, which is a division of Ser. No. 450,967, Mar. 14, 1974, Pat. No. 3,983,055.

[51] Int. Cl.² .............................................. C07C 1/04
[52] U.S. Cl. .............................. 260/449 M; 252/432; 252/437; 252/441; 252/454; 252/455 R; 252/456; 252/459; 252/460; 252/455 Z; 260/449.6 M; 260/449.6 R; 260/449 R; 260/596; 260/683.9; 423/336
[58] Field of Search ........... 260/449 M, 449.6, 449 R, 260/449.6 M

[56] References Cited

U.S. PATENT DOCUMENTS 3,983,055  9/1976  Mitchell et al. ...................... 252/454

*Primary Examiner*—Howard T. Mars
*Attorney, Agent, or Firm*—Charles A. Huggett; Raymond W. Barclay; Dennis P. Santini

[57] ABSTRACT

Hydrogenation-dehydrogenation of suitable feedstock is provided wherein such feedstock is subjected to hydrogenation-dehydration conditions in the presence of a catalytic amount of a solid containing, at least in part, a synthetic amorphous solid prepared by hydrolyzing and polymerizing in the presence of water a silane having the formula $R(Si)X_3$, wherein R is a nonhydrolyzable organic group, X is a hydrolyzable group and (Si) is selected from the group consisting of

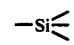

and

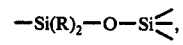

and calcining the polymerized product, said silane being admixed with a second compound, $R'_nMY_m$, wherein R' is selected from the group consisting of the same groups as R, Y is selected from the group consisting of the same groups as X and oxygen, M is at least one member selected from the group consisting of the elements of Groups IIIA, IVA, IVB, VA, VB, VIB, VIIB and VIII of the Periodic Table, m is any number greater than 0 and up to 8 and n is from 0 to any number less than 8.

18 Claims, No Drawings

METHANATION OVER SYNTHETIC AMORPHOUS SILICAS

CROSS-REFERENCE

This is a continuation-in-part of application Ser. No. 638,405, filed December 8, 1975, now U.S. Pat No. 4,003,825, filed March 14, 1974, now U.S. Pat. No. 3,983,055.

BACKGROUND OF THE INVENTION (1) Field of the Invention

This invention relates to use of specifically prepared amorphous synthetic siliceous materials, as catalysts in hydrogenation-dehydrogenation of suitable chemical feedstock. Such feedstock for hydrogenation may be any unsaturated hydrocarbons, e.g. isobutene; or organic compounds containing carbonyl groups, e.g. aldehydes, ketones, $CO_2$ or CO. Such feedstock for dehydrogenation may be any saturated or partially unsaturated hydrocarbons, especially paraffins, olefins or naphthenes; or alcohols of from 1 to about 10 carbon atoms.

(2) Description of the Prior Art

U.S. Pat. No. 2,441,214 discloses a hydrocarbon conversion catalyst prepared by reacting an aluminum, magnesium or zirconium compound, such as $AlCl_3$, with dehydration product of a silanol or siloxane polymer $R_3SiOSiR_3$,

or

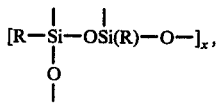

R being alkyl, aryl or aralkyl, to produce a metal complex, precipitating in water plus base ($NH_4OH$), water-washing and drying. In one example, the product was calcined for 3 hours at 500° C. This procedure is not the same as that utilized in the present invention, and it results in loss of silicon values with lower surface area and fewer small pores than desirable.

U.S. Pat. No. 2,483,963 discloses the hydrolysis of organochlorosilanes to produce organosiloxanes. The process involves introducing liquid silane into the upper end of a silane-water vapor contact zone and removing a condensed siloxane. The amount of water used is in excess of that necessary to hydrolyze the silane. The trichloro, $RSiCl_3$, in which R is alkyl or aryl, is either not used at all or used in a restricted amount so that in the formula $RnSiCl_{4-n}$, n is at least 1.7.

In U.S. Pat. No. 2,722,504 is disclosed a catalyst material having components of an activated silica or alumina, an oxide or sulfide of certain transition metals and an organophilic silicone coating formed by (1) adsorbing onto the activated surface of the first component a silane monomer of the formula

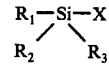

wherein X is a hydrolyzable group, $R_1$ is non-hydrolyzable and $R_2$ and $R_3$ may each be hydrolyzable or not, (2) hydrolyzing the monomer, then (3) heating the combined materials at 800° to 1200° F to dry; the second metal component is added by impregnation, or alternatively is added with the silane monomer.

In U.S. Pat. No. 3,661,770 there is disclosed a method of preparing a catalyst by using a chlorosilane compound, $SiX_4$, at least one of the X's being chlorine and the others hydrogen, methyl, ethyl, methoxy and ethoxy with a Group VIII metal-alumina composite at a temperature of 500° to 900° F. The composite is the catalyst and the silane is an activating agent.

SUMMARY OF THE INVENTION

It has now been discovered that shape-selectivity or the pore-size distribution of a silica or silica-containing composition may be controlled by the steps of (1) hydrolyzing a mono-organo silane, $R(Si)X_3$, alone or in the presence of other compounds having the formula $R'_nMY_m$, wherein the R groups and R' groups are organic non-hydrolyzable groups and may be the same or different, X is a hydrolyzable group, Y is the same as X or oxygen, and M is either a metal or non-metal of the groups of the Periodic Table including silicon other than Groups IA, IIA, VIIA and O, m is a number up to 8 and n is zero or a number less than 8, or an inorganic ionic compound containing M and Y, (2) bringing about the condensation and polymerization of the hydrolyzed compounds and (3) calcining the polymerized product. It has further been discovered that the calcined silica-containing products above have utility in a process for hydrogenation-dehydrogenation of suitable organic compound feedstocks, such as, for example, hydrogenation of unsaturated hydrocarbon compounds; organic compounds containing carbonyl groups, including ketones and aldehydes; CO and $CO_2$; and dehydrogenation of saturated or partially unsaturated hydrocarbon compounds, including naphthenes, paraffins and olefins. The hydrogenation of CO or $CO_2$ is commonly referred to as methanation.

In the following discussion, "silica products" or "silica structures" and similar terms are intended to include materials as described herein, containing components other than silica alone. Also as used herein, the term "hydrolyzable" refers to any group which is capable of conversion to hydroxy in the presence of water under conditions of the hydrolysis step; "non-hydrolyzable" refers to any group which does not convert to hydroxy under the said conditions.

DESCRIPTION OF SPECIFIC EMBODIMENTS

This invention provides a hydrogenation-dehydrogenation process utilizing as a catalyst a solid having shape-selectivity for hydrocarbon conversion and other processes but without the cost of many of the known shape-selective catalysts. The present invention provides inexpensive catalysts of controlled pore size whose adsorptive characteristics can be designed to accept within the pores thereof hydrocarbon molecules of different shapes. Furthermore, this invention provides a silica structure which may be used alone as a catalyst or as the selective carrier for more active components.

Formation of the silica structures for use in this invention is carried out by the steps of hydrolyzing the silane, polymerizing the hydrolysis products and calcining the polymerized product. The silanes used in formation of the silica structures useful in this invention have the formula $R(Si)X_3$ wherein R is an organic radical which cannot be hydrolyzed in the above hydrolyzing step and X is a hydrolyzable group which ultimately converts the silane to a siloxane polymer. As used in this invention, R may be alkyl, cycloalkyl, alkenyl, cycloalkenyl, aryl, alkaryl, aralkyl, or a heterocyclic group containing oxygen, sulfur or nitrogen in the ring, aminoalkyl (including polyamino alkyl), and the halo and hydroxy derivatives of such groups, R having preferably from 1 to about 40 carbon atoms; the expression (Si) may be a single silicon atom or

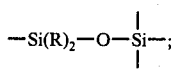

X may be halogen, hydrogen, alkoxy, aryloxy, of from 1 to about 20 carbon atoms, alkali metaloxy, carboxy, nitro, amino and the like. The preferred compounds useful in forming the silica structure for use in this invention are those in which R is alkyl or aryl or a group containing one or more amino groups and X is halogen or alkoxy. Non-limiting examples of R include methyl, ethyl, butyl, hexyl, decyl, dodecyl, octadecyl, phenyl, tolyl, naphthyl, aminomethyl, aminoethyl, aminopropyl, ethylenediaminomethyl, ethylenediaminopropyl, cyclohexyl, chlorobutyl, hydroxybutyl, ethoxyethyl, propoxypropyl and the like. Non-limiting examples of X include chloro, bromo, iodo, methoxy, ethoxy, acetoxy and the like.

Normally hydrolysis would convert hydrolyzable groups to hydroxy. However, trihydroxy organosilanes would lead instead to organosiloxane polymers by dehydrocondensation. Molecular weights ranging from 2500 to 3,000,000 or more are usually obtained.

Depending on the amount of water present in the hydrolysis reaction mixture and the type of R group, the intermediate polymerization product is either a three-dimensional cage-containing structure or a two-dimensional linear or sheet-containing structure. The cage-containing structure is the preferred structure in this invention for producing the more desirable silica, although it is likely that the hydrolysis step produces both types of polymer in the same reaction mixture. For this reason, the amount of water used in the hydrolysis is preferably kept to the stoichiometric amount or slightly in excess of that necessary to convert the X groups to hydroxy. It is preferred to use a system of an organic solvent and water instead of water alone. Excess water also has been found to affect the distribution of the pore sizes in the finished calcined product. It is preferred to use 0.5:1 to 10:1 by volume of organic solvent to water. The preferred solvents are hydrocarbons, e.g. hexane and benzene, ethers and alcohols, the preferred alcohols being methanol, ethanol and other lower alcohols. However, solubility of the silane in the water-solvent system is not necessary, providing the water-control is maintained throughout the hydrolysis step. Hence, any convenient solvent system is useful.

The silane is added to the solvent-water mixture and stirred. An acid or base hydrolysis/condensation catalyst may be used. Hydrolysis may be effected at a temperature as low as room temperature and up to about 200° C. Usually a solid precipitate or a thick syrup is produced. The precipitated polymer may be separated from the reaction mixture by filtration. The semi-solid polymer may be separated by boiling off the liquids preferably under vacuum. The remaining structure is understood to consist of the following repeating group:

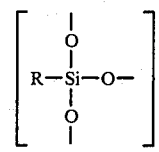

If the silane is hydrolyzed alone, without a second dissimilar component present, the polymeric structure is understood to be primarily a cage-type three-dimensional network molecule. Other silanes may be present in the hydrolysis step. Other tri-X silanes of different R groups or mono-X or di-X silanes of the same or different R groups will provide a cage molecule of differing channels or pore characteristics. Generally, the R group determines the size of the pores of the final product, the smaller the R group the smaller the pore.

The siloxane polymer resulting from the hydrolysis step is then subjected to stepwise or programmed calcining. Essentially, calcining replaces the R groups of the polymer with hydroxy, or oxy groups depending upon whether pairs of hydroxy groups are formed close enough to each other to condense or, if calcining is done in the absence of air, hydrogen. Clearly the gaps caused by the removed R groups form the small pores. Calcining is carried out at the minimum elevated temperature necessary to remove the R groups, normally from about 200° C below the sintering temperature, usually 200° to 600° C, preferably from 350° to 550° C, and at rates of increase from 10° C to 300° C per hour, preferably 20° to 250° C (or from 0.3° to about 4° C per minute).

When the calcining step is carried out in air, hydroxy or oxy or even —M—O— groups (if a second component is present) occur in the product. In the absence of air, it is believed that

groups occur by free radical mechanism.

Preparation of a small pore size material with a high degree of cross-linking (three-dimensional structure) may be obtained by using $R(Si)X_3$ alone or with other silanes in which R is a low alkyl. Some selectivity for particular hydrocarbon molecules to be sorbed, otherwise obtainable with $R(Si)X_3$, may be lost in final products obtained when $SiX_4$, $R_2(Si)X_2$ or $R_3(Si)X$ are in the initial reaction mixture. Since control of shape selectivity is one of the desirable ends of this invention, as well as producing stable three-dimensional structures, it is most preferred that the $R(Si)X_3$ be the only silicon reactant; if a mixture of silanes is used, it is preferred that at least about 33% by weight of the silanes be $R(Si)X_3$. For example, a product derived from phenyl trichlorosilane has a slightly lower pore volume than that of a product obtained from a mixture of 80% phenyl trichlorosilane and 20% diphenyl dichlorosilane, but the selectivity for n-hexane was higher in the first product.

Surface areas also vary with R, methyl producing a relatively low area, bulkier groups such as cyclohexyl or phenyl producing products of over 300 m$^2$/g.

The R(Si)X$_3$ silane may be hydrolyzed in the presence of R'$_n$MY$_m$, in which R' is the same as or different from R, Y is any combining group, preferably halogen or alkoxy, aryloxy, metaloxy, hydroxy or oxy, M is a metal or non-metal, preferably of Periodic Groups IIIA, IVA, IVB, VA, VB, VIB, VIIB and VIII, $m$ is a number up to 8, and $n$ is 0 or a number less than 8. In addition, inorganic ionic compounds consisting of an anion of M and Y with a cationic portion may be used. Suitable cations include hydrogen, alkali and alkaline earth metals and ammonium. An M-containing compound may also be a complex having as one ligand a suitable group such as amine or phosphine which latter is part of an R group on silicon. In particular, the amorphous silica solids of this invention may have incorporated therewith zirconium, thorium, chromium, iron, molybdenum, rhodium, tungsten, copper, tin, titanium, vanadium, cobalt, nickel, zinc, silver, ruthenium, palladium, platinum, and the like, and mixtures thereof with each other and/or with aluminum.

The second component is combined with the R(Si)X$_3$ in a solvent system in the hydrolysis step. These combination products, as with the silica products alone, are also amorphous solids of varying pore sizes and surface areas.

The silane is combined with one or more members of the second component in the presence of water and solvent, again water being in preferably stoichiometric, or only slightly over stoichiometric amounts. If necessary a small quantity of a base acting as a catalyst for promoting the polymerization of the mixture may be present, such as pyridine, pyrimidine, triethylamine or ammonia. The resulting solid is removed and subjected to calcination to produce the desired material.

Such compounds as aluminum chloride, aluminum butoxide, aluminum ethoxide, aluminum propoxide, sodium aluminate, ethyl aluminum chloride, methyl aluminum chloride, boric acid, sodium borate, methyl borate, cobalt chloride, nickel chloride, nickel acetate, phenyl phosphite or phosphonate, butyl phosphonate, phenyl dichlorophosphine, palladium chloride, methylamine palladium chloride, palladium nitrate, chloroplatinic acid, potassium chloroplatinate, cyclooctadienyl platinum dichloride, butyl tin acetate, tin chloride, dicyclopentadienyl titanium chloride, titanium chloride, vanadium chloride, vanadium oxide are suitable as the second component in this invention. Second components containing Group VIII metals, such as, for example, iron, nickel, cobalt, platinum and/or palladium, are preferred. Particularly preferred second components are those containing the mixtures of one or more Group VIII metals with aluminum.

In addition, known methods of exchange or impregnation can be used to incorporate additional metals for the purpose of producing catalysts.

In general, unsaturated hydrocarbon compounds or organic compounds containing one or more carbonyl groups may be catalytically hydrogenated in the presence of a catalytically effective amount of the above-defined specifically prepared amorphous synthetic siliceous material over a range of catalytic hydrogenation conditions, including a temperature of from about 0° to about 400° C, preferably from about 25° to about 250° C, a pressure of from about 1 atmosphere to about 25 atmospheres, preferably from about 5 to about 10 atmospheres, a hydrogen/feedstock mole ratio of from about 2 to about 100, preferably from about 18 to about 75, and a liquid hourly space velocity (LHSV) of from about 0.1 hr.$^{-2}$ to about 100 hr.$^{-1}$, preferably from about 0.5 hr.$^{-1}$ to about 75 hr.$^{-1}$. The hydrogen circulation for this reaction depends, of course, upon the particular feedstock being hydrogenated and may vary from about 2000 scf/bbl to about 15,000 scf/bbl, preferably from about 7,000 scf/bbl to about 12,000 scf/bbl.

When hydrogenation is conducted for a feedstock comprising essentially CO or CO$_2$, the temperature must be maintained at from about 250° to about 700° C, preferably from about 300° to about 600° C, the pressure must be maintained at from about 1 atmosphere to about 150 atmospheres, preferably from about 1 atmosphere to about 10 atmospheres, the hydrogen/CO or CO$_2$ feedstock mole ratio must be maintained at from about 1 to about 10, preferably from about 2 to about 4, and the gas hourly space velocity (GHSV), expressed at standard temperature and pressure, must be maintained at from about 5000 hr.$^{-1}$ to about 100,000 hr.$^{-1}$, preferably from about 6,000 hr.$^{-1}$ to about 60,000 hr.$^{-1}$. Excess hydrogen is supplied to this reaction.

Further, when dehydrogenation is conducted for a feedstock comprising essentially a saturated or partially unsaturated hydrocarbon, e.g. paraffin, olefin or naphthene, a temperature of from about 200° to about 750° C, preferably from about 500° to about 700° C, a pressure of from about 0.1 atmosphere to about 25 atmospheres, preferably from about 0.2 to about 3 atmospheres, and a LHSV of from about 0.1 hr.$^{-1}$ to about 10 hr.$^{-1}$, preferably from about 1 hr.$^{-1}$ to about 3 hr.$^{-1}$, must be maintained.

When dehydrogenation is conducted for a feedstock comprising an alcohol of from 2 to about 10 carbon atoms, e.g. ethanol, isopropanol and others, the temperature must be maintained at from about 200° to about 500° C, preferably from about 250° to about 400° C, the pressure must be maintained at from about 0.5 atmosphere to about 2 atmospheres, preferably at about 1 atmosphere, and the liquid hourly space velocity (LHSV) must be maintained at from about 0.1 hr.$^{-1}$ to about 10 hr.$^{-1}$, preferably from about 0.5 hr.$^{-1}$ to about 5 hr.$^{-1}$. When dehydrogenation is conducted for a feedstock comprising methanol, however, the temperature should be maintained at from about 300° to about 500° C, preferably from about 350° to about 400° C and the pressure and LHSV may be maintained as for dehydrogenation of alcohol feedstock of from 2 to about 10 carbon atoms.

The following examples represent illustrations of the present invention and are not meant to be limitations thereof. Unless otherwise expressed, amounts and percentages are on a weight basis. Percent yields of the final calcined products are based on the weight of the polymer produced after hydrolysis and polymerization.

EXAMPLE 1

In a suitable vessel was added 25 ml of phenyl trichlorosilane to a solution of 15 ml of water and 60 ml of methanol (1:4 v/v). The heat generated by this addition brought this mixture to boiling and a white solid formed. The mixture was maintained at room temperature for four days, after which the solid was removed and washed in ethanol and air dried. The washed solid was calcined in air by heating at 100° per hour to 500° C and held at that temperature for 10 hours.

The resulting product was amorphous by X-ray examination and had the following characteristics:

| | |
|---|---|
| Surface Area: | 511 m$^2$/gm |
| Mean Pore Diameter: | 26 A |
| Pore Volume: | 0.341 ml/gm |
| Particle Density: | 1.28 g/ml |
| Real Density: | 2.32 g/ml |

| Pore Size Distribution | |
|---|---|
| less than 7 A | 61.0% |
| 7 – 10 | 8.0 |
| 10 – 15 | 3.4 |
| 15 – 25 | 1.4 |
| 25 – 300 | 2.1 |
| over 300 | 24.1 |

EXAMPLE 2

In a suitable reactor, 50.4 grams of $H_2NCH_2CH_2NHCH_2CH_2CH_2Si(OCH_3)_3$ was added to 150 ml of the 4/1 v/v methanol-water mixture of Example 1. The mixture was stirred for one hour and allowed to stand for one day. The mixture was then refluxed for 2 hours and the solvent removed under vacuum. The resulting product was calcined at 3° C per minute to 538° C and held for 10 hours and then cooled. The yield was 35% by weight based on the weight of polymer. The product had a surface area of 642 m$^2$/gram.

EXAMPLE 3

In a suitable reactor, 50 grams of $BrCH_2CH(Br)SiCl_3$ was added to 150 ml of the 4:1 v/v methanol-water solvent. The mixture was allowed to stand for 2 days. It was refluxed for 2 hours and filtered. The solids were washed with three 200-ml portions of ethanol and dried in a vacuum oven at 125° C for 2 hours. The product was calcined by heating at 1° C per minute to 538° C, and held at that temperature for 10 hours, and finally cooled. The yield was 27% by weight and the product had a pore volume of 0.15 ml/g, surface area of 242 m$^2$/g and a particle density of 1.66 g/ml.

EXAMPLE 4

In a suitable reactor, 50.5 grams of dodecyltrichlorosilane $C_{12}H_{25}SiCl_3$ was added to 150 ml of the methanol-water 4/1 v/v solvent and the mixture was allowed to stand for 4 days. The mixture was then refluxed at about 60° C for 2 hours. The product polymer was a viscous liquid. The solvent was decanted and polymer washed three times with 200-ml ethanol portions with decanting of the wash each time. The washed product was dried in a vacuum oven at 120° C for 2 hours, calcined at 1° C per minute to 538° C, held at that temperature for 10 hours and cooled. The yield was 20% by weight of a product having the following characteristics: pore volume 0.233 ml/g, surface area 178 m$^2$/g and particle density 1.59 g/ml.

EXAMPLE 5

A mixture of 55 grams of triphenylhydroxy silane, $(C_6H_5)_3SiOH$, 8 grams of sodium and 300 ml of benzene was refluxed at 80° C for 3 hours and allowed to stand without heat for 5 days. The mixture was cooled to about 10° C in an ice bath and stirred, and 40 grams of $SiCl_4$ in 200 ml benzene was added. The resulting mixture was subjected to reflux at 80° C for 2 hours and cooled. During the $SiCl_4$ addition and refluxing, a stream of helium was passed through the reactor to exclude moisture. The reaction mixture was filtered to remove solid by-product. The benzene was then removed on a ratary evaporator to leave 39.7 grams of the product $(C_6H_5)_3$-Si-O-SiCl$_3$.

In a suitable reactor, 29.6 grams of the above product was added to 150 ml of the same methanol-water solvent and the mixture was allowed to stand one day. The mixture was then refluxed at 60° C for 2 hours and cooled and allowed to stand for 7 days. The viscous white liquid was separated from the supernatant solvent, washed three times with 200-ml portions of ethanol. After the first wash, the product was a granular solid. The washed product was dried in a vacuum oven at 120° C for 2 hours and calcined at 1° C per minute to 538° C, being held at that temperature for 10 hours. The yield was 23% by weight; pore volume 0.21 ml/g, surface area 341 m$^2$g, particle density 1.59 g/ml.

EXAMPLE 6

In a suitable reactor, 25 grams of phenyl trichlorosilane and 25 grams of methyl trichlorosilane was added to 150 ml of the 4/1 methanol-water solvent. The mixture was allowed to stand for 2 hours and then refluxed for 2 hours. The solvent was decanted and the white solid washed three times with 100-ml portions of water, three times with 100-ml portions of acetone and three times with 100-ml portions of hexane. The product was dried in a vacuum oven at 118° C for 1.5 hours then calcined as in Example 5. The yield was 62% by weight; surface area 355 m$^2$/g.

EXAMPLE 7

A silica compound prepared as in Example 2 was produced by adding to 150 ml of a 4/1 v/v mixture of methanol and water 10 grams of $SiCl_4$, 4 grams of methyl trichlorosilane, 33.5 grams of dimethyl dichlorosilane and 2 grams of trimethyl chlorosilane. The calcination yielded 66% by weight of final product. This product had a pore volume of 0.70 ml/g, a surface area of 94 m$^2$/g and a particle density of 0.8 g/ml.

EXAMPLE 8

In a suitable reactor 42 grams of phenyl trichlorosilane and 10.3 grams of diphenyl dichlorosilane were added to 150 ml of the 4/1 by volume methanol-water solvent. The mixture was allowed to stand for 6 days. The solvent was decanted and the product was washed three times with 300-ml portions of ethanol. The product was dried in a vacuum oven for 16 hours and calcined as in Example 5. the yield was 27% by weight.

EXAMPLE 9

In a suitable reactor, 100 ml of ethyl trichlorosilane was added to 300 ml of the same methanol-water solvent mixture of the previous examples. The mixture was allowed to stand for 10 days, then heated to reflux for one-half hour and again allowed to stand for 2 days. The solvent was boiled off over a 2-hour period and the product was washed three times with 100-ml portions of ethanol and three times with 100-ml portions of petroleum ether. The product was air-dried, calcined at 9°C per minute to 538° C held at that temperature for 10 hours and then cooled. The yield was 73% by weight;

pore volume 0.22 ml/g, surface area 90 m²/g and particle density 1.44 g/ml.

EXAMPLE 10

In a suitable reactor 50 grams of methyl trichlorosilane was mixed with 150 ml of the 4/1 v/v methanol-water solvent. The mixture was allowed to stand for 7 days. The solvent was decanted and the product washed three times with 100-ml portions of ethanol. The product was dried in a vacuum oven at 120° C for one hour and calcined as in Example 5. The yield was 85%, pore volume 0.16 ml/g, surface area 28 m²/g and particle density 1.62 g/ml.

A number of silica products were tested for sorption capacity in the following manner. A sample solid of known weight is placed in a quartz basket suspended from a microbalance (Cahn Instrument Co.) on a quartz rod, all enclosed in a jacketed heater. A carrier gas, helium, is passed through a wick saturator to entrain water or hydrocarbon vapor and then into the microbalance and basket at 100 ml/min. Temperature and weight measurements of the solid are continuously made. The temperature is maintained at 35° C in the heater. The sorption capacities are reported at partial pressures in the carriage stream of 20 mm. Hg for hydrocarbons, 12 mm. for water. The following are results for sorption of n-hexane, 2,3-dimethylbutane, water, cyclohexane, benzene and triethylamine. For comparison purposes, an aluminosilicate zeolite catalyst of the ZSM-5 type, described in U.S. Pat. No. 3,702,886, in which the cations are predominantly hydrogen (herein referred to as "HZSM-5"), was also measured for sorption capacity.

| Example | $nC_6$ | 2,3-DMB | $H_2O$ | $CycC_6$ | $C_6H_6$ | TEA |
|---------|--------|---------|--------|----------|----------|------|
| 1 | 0.17 | 0.13 | 0.15 | 0.13 | 0.17 | 0.05 |
| 2 | 0.32 | 0.27 | 0.27 | — | — | — |
| 3 | 0.13 | 0.06 | 0.10 | — | — | — |
| 4 | 0.09 | 0.02 | 0.10 | 0.04 | 0.09 | — |
| 8 | 0.10 | 0.11 | 0.16 | — | — | — |
| 9 | 0.09 | 0.01 | 0.12 | 0.06 | 0.07 | — |
| 10 | 0.008 | 0.006 | 0.005 | — | — | — |
| HZSM-5 | 0.19 | 0.16 | 0.09 | — | — | 0.12 |

EXAMPLE 11

To a solution of 50 grams of phenyl trimethoxysilane, $C_6H_5Si(OCH_3)_3$, and 10 ml of pyridine in 150 ml of 4:1 methanol water v/v mixture were added 5 grams of aluminum t-butoxide $Al(O\text{-}t\text{-}C_4H_9)_3$. The mixture was allowed to stand overnight and was then heated to reflux at about 60° C for 6 hours. Upon cooling the mixture, a solid precipitated. The solid was filtered out, washed with ethanol, dried in a vacuum oven and heated to 538° C at 1° C/minute in an air stream. It was then cooled yielding 11.3 grams of a brown-gray aluminum-silicon solid.

EXAMPLE 12

In a suitable reactor 31.3 grams of ethyl trichlorosilane, $CH_3CH_2SiCl_3$, 150 ml of the 4:1 methanol-water mixture and 3 grams of 1,5-cyclooctadienyl platinum dichloride were combined. Heat evolved and the mixture became opaque. After standing overnight, the light yellow solid and clear liquid so resulting were refluxed at about 60° C for 16 hours and cooled. The solid was filtered out, washed and dried and calcined as in Example 11, leaving 8.8 grams of a black granular platinum-silicon product.

EXAMPLE 13

To a vessel containing 750 ml of water was added 82.9 grams of methyl trichlorosilane, the temperature rising to 56° C. The mixture was stirred for 10 minutes and a white solid precipitate was filtered out, water washed and added to a solution of 20.2 grams of NaOH (equimolar to silicon) in 63 grams of water. The resulting mixture was stirred for 2 hours at 100° C, then 168 grams of methanol was added. Minor solid matter was removed by filtration, leaving as filtrate an aqueous solution of $CH_3Si(OH)_2ONA$. To this solution were added 24 grams of nickel chloride hexahydrate and 13.3 grams of aluminum chloride (equimolar amounts) dissolved in 150 ml of the 4:1 alcohol:water mixture. A light green solid precipitated; an additional 150 ml of solvent mixture was added and the system was heated to reflux at about 70° C for 2 hours. The solid product was separated from the supernatant liquid after standing for 16 hours at room temperature. Sodium chloride was removed with boiling water and methanol, and the washed solid was dried in vacuum at 120° C. The product was calcined as in Example 11, providing a yield of 38.6 grams of a light tan nickel-aluminum-silicon solid.

EXAMPLE 14

To a vessel containing 200 ml of absolute ethanol were added 0.839 grams of $PdCl_2$ and 51.6 grams of aminoethylaminopropyl trimethoxysilane (the $H_2NCH_2CH_2NHCH_2CH_2CH_2Si(OCH_3)_3$ of Example 2). After standing overnight the mixture was filtered to remove solid $PdCl_2$ particles and 50 ml of water was added producing a light yellow solution. No precipitate formed after 5 days of standing; the solvent was removed under vacuum, below 33° C, leaving a light yellow solid. The solid was calcined as in the previous examples; 14.3 grams of a red-brown palladium-silicon solid was produced containing about 3% palladium.

EXAMPLE 15

In a suitable reactor, 10 grams of aluminum triisopropoxide and 50.6 grams of $H_2NCH_2CH_2NHCH_2CH_2Ch_2Si(OCH_3)_3$ were added to 150 ml of the 4/1 methanol-water solvent and allowed to stand one day. The mixture was refluxed at 60° C for 2 hours and allowed to stand one more day. It was again refluxed for 96 hours. A liter of methanol was added and the mixture was heated to boiling, then filtered while hot. The solvent was removed from the filtrate with a rotary evaporator, dried in a vacuum oven at 120° C for 4 hours, then calcined as in Example 11. The yield was 51.2%.

EXAMPLE 16

In a suitable reactor 50.9 grams of $H_2NCH_2CH_2NHCH_2CH_2CH_2SI(OCH_3)_3$, 3.35 grams of aluminum tri-ethoxide and 10 ml of pyridine were mixed with 50 ml $H_2O$ and 200 ml of methanol and the mixture was heated to reflux for 16 hours. The solvent was stripped under vacuum and the product was calcined at 3° C per minute to 538° C, held at that temperature for 10 hours and cooled. The yield was approximately 47%.

EXAMPLE 17

In a suitable reactor, 50 grams of phenyl trichlorosilane and 15 grams of boric acid were added to 150 ml of tetrahydrofuran. The mixture was stirred for 2 hours, refluxed for 2 hours and allowed to stand for 48 hours. The solvent was stripped off with the rotary evaporator under house vacuum at 100° C. The product was calcined as in Example 16, but at a rate of 2° C per minute. The yield was 34%.

EXAMPLE 18

In a suitable reactor, 10 ml of phenyl trimethoxysilane, $C_6H_5Si(OCH_3)_3$, 5 grams of vanadium oxy acetylacetonate, 200 ml methanol, 25 ml of water and 5 ml of triethylamine were mixed together and allowed to stand for 10 days. The resulting product was filtered out and washed three times with 100-ml portions of methanol, dried in a vacuum oven at 120° C for 2 hours. The washed product was calcined at 1° C per minute to 538° C, held at that temperature for 10 hours. The yield of vanadium-silicon product was about 50.4% by weight.

EXAMPLE 19

In a suitable reactor, 10 ml of methyl trichlorosilane, 5 ml of dibutyl tin diacetate, 200 ml of methanol and 25 ml of water were mixed and allowed to stand for 10 days. The product was treated as in Example 18. The yield of tin-silicon product was about 67% by weight.

EXAMPLE 20

In a suitable reactor were mixed 33 grams of phenyl trichlorosilane and 40 grams of phenyl phosphonic acid in 30 ml of methanol and the mixture was refluxed for 16 hours. The solvent was removed under vacuum on a rotary evaporator. The product was an amber viscous material; it was dissolved in 100 ml of boiling acetone. The acetone was removed by evaporation leaving solid product. Calcining at 3° C per minute to 538° C, holding for 10 hours at that temperature left a 33.8% yield of phosphorus-silicon product.

EXAMPLE 21

In a suitable reactor were mixed 94.1 grams of phenyl trichlorosilane, 3.34 ml of a solution of 0.113 gram/ml of sodium ethyl chloroplatinate in ethanol and 15.8 grams of phenyl dichlorophosphine. Slowly added dropwise to the mixture was 200 ml of 1/1 by volume methanol-water mixture. Foaming and a heavy white precipitate resulted. The product was filtered out, washed with about 2000 ml of methanol and calcined as in Example 18. A 25% yield of phosphorus-platinum-silicon product was obtained.

EXAMPLE 22

A solution of $CH_3Si(OH)_2ONa$, prepared as in Example 13, was mixed with 24.1 grams of $CoCl_2.6H_2O$ and 13.3 grams of aluminum chloride dissolved in 150 ml of the 4/1 v/v methanol-water solvent. Another 150-ml solvent portion was added, the mixture was refluxed for 2 hours and then cooled. Solids were filtered out, and 1000 ml of boiling water was passed through the filter paper to remove NaCl. The solids were washed three times with 500-ml portions of methanol, dried in a vacuum oven at 120° C for 16 hours and calcined at 3° C per minute to 500° C, being held at that temperature for 10 hours, and finally cooled. The yield of cobalt-aluminum-silicon product was 84.4%.

The physical characteristics of the products of Examples 11 to 22 are as follows:

| Product of Example | Percent of M | | Pore Volume ml/g | Surface Area, m²/g | Particle Density, g/ml |
|---|---|---|---|---|---|
| 11 | 6.3 | (Al) | 0.284 | 334 | 1.52 |
| 12 | 3.19 | (Pt) | 0.086 | 117 | 1.94 |
| 13 | 13.2 | (Ni) | — | — | — |
| | 6.8 | (Al) | 1.43 | 240 | 0.56 |
| 14 | 3.0 | (Pd) | 0.512 | 832 | 1.06 |
| 15 | 9.7 | (Al) | — | 52 | — |
| 16 | 1.1 | (Al) | — | 296 | — |
| 17 | 7.72 | (B) | — | below 5 | — |
| 18 | 0.22 | (V) | — | — | — |
| 19 | 0.1 to 1.0 | (Sn) | — | — | — |
| 20 | 24.0 | (P) | 1.345 | 35 | 0.542 |
| 21 | 0.5 | (P) | — | — | — |
| | 0.02 | (Pt) | — | 354 | — |
| 22 | 15.2 | (Co) | 1.030 | 191 | 0.740 |

EXAMPLE 23

The product catalyst of Example 14 was used in this process in which isobutene was hydrogenated. The sample of solid catalyst used contained 3% Pd and had a surface area of 799 m²/gm and a pore volume of 0.512 ml/gm. The procedure of the reaction was as follows: A 100-mg (0.25 ml) sample was placed in a vertical glass tube and treated with $H_2$ at 138° C and atmospheric pressure. A second stream of isobutene was added and, after 0.5 minute, a sample of the product stream was analyzed by gas chromatography.

At a temperature of 138° C with a feed of hydrogen and isobutene in a mole ratio of 75:1, at a LHSV of 72 and one atmosphere pressure, conversion of 94.8% was obtained.

EXAMPLE 24

A sample of 11.5 mg of the Example 13 catalyst was heated at 538° C in excess hydrogen gas in the Cahn microbalance and carbon monoxide was introduced to produce a mole ratio of 3.9:1 $H_2$:CO, at a GHSV of 54,500 (expressed at standard temperature and pressure) and at atmospheric pressure. The weight of catalyst could be measured during the run and it increased by 22% in 30 minutes. The major product gas component was methane with a CO conversion of 10%. Minor amounts of ethane, propane and $CO_2$ were also formed. In another run, in a conventional fixed bed stainless steel reactor, at 42.6 atmospheres, using 1 ml of 20–30 mesh of the catalyst of Example 13 with 21.5 ml of Vycor chips, and a 4/1 mole ratio of $H_2CO$ feed at a GHSV of 10,000 (expressed at standard temperature and pressure). The results were as follows:

| Duration, hrs. | Temp. ° C | %C as $CH_4$ in Product |
|---|---|---|
| 4 | 250 | 1.4 |
| 4.6 | 300 | 4.8 |
| 7 | 350 | 8.8 |
| 7.7 | 400 | 12.4 |

For comparison a similar pressure reaction was run using as catalyst 1 ml 20–30 mesh Ni-0104 (a 60% Ni/-kieselguhr made by The Harshaw Chemical Co. and recommended as a methanation catalyst). The results were as follows:

| Duration, hrs. | Temp. ° C | %C as $CH_4$ in Product |
|---|---|---|
| 1.5 | 250 | 0.2 |

-continued

| Duration, hrs. | Temp. °C | %C as $CH_4$ in Product |
|---|---|---|
| 2.5 | 350 | 4.5 |
| 3.5 | 400 | 4.5 |
| 5.0 | 450 | 8.3 |

Therefore, it is noted that the catalyst of Example 13 is more active in hydrogenation of CO than the above commercial methanation catalyst.

EXAMPLE 25

In this example, a quantity of isopropanol is passed over a fixed bed of 12 mg of a catalyst prepared as in Example 13 at 350° C, one atmosphere pressure and an LHSV of 1 hr$^{-1}$. The dehydrogenation product obtained is acetone.

As indicated previously, the silica structures of this invention may be controlled to have shape selectivity toward certain hydrocarbon molecules. One desirable small pore size distribution will accept normal molecules and exclude branched isomers. The incorporated components with the silica do not effect this shape selectivity adversely. Pore size distributions (in percent) are as follows:

| Pore Radius, A | Ex. 11 | Ex. 12 | Ex. 14 |
|---|---|---|---|
| below 7 | 35.7% | 24.6 | 0.0 |
| 7–10 | 8.4 | 18.9 | 50.8 |
| 10–15 | 1.6 | 26.4 | 27.2 |
| 15–25 | 0.3 | 2.4 | 2.3 |
| 25–50 | 0.0 | 3.3 | 0.3 |
| 50–75 | 0.0 | 2.9 | 0.4 |
| 75–100 | 0.0 | 2.4 | 0.2 |
| 100–200 | 0.0 | 4.0 | 0.3 |
| 200–300 | 0.0 | 1.1 | 0.2 |
| over 300 | 54.0 | 14.0 | 18.3 |
| Total Vol. | 0.284 | 0.086 | 0.512 |
| Vol. below 15 A | 0.130 | 0.060 | 0.399 |

We claim:

1. A process comprising (1) contacting a feedstock selected from the group consisting of carbon monoxide and carbon dioxide with a solid catalyst material in the presence of hydrogen and under process conditions including a temperature of from about 250° to about 700° C, a pressure of from about 1 atmosphere to about 150 atmospheres, a gas hourly space velocity, expressed at standard temperature and pressure, of from about 5,000 hr$^{-1}$ to about 100,000 hr$^{-1}$ and a hydrogen/feedstock mole ratio of from about 1 to about 10 and (2) recovering a product containing methane, said solid catalyst material containing a synthetic amorphous solid prepared by the steps of hydrolyzing and polymerizing at a temperature of up to about 200° C in the presence of water a silane having the formula R(Si)X$_3$, wherein R is an organic radical selected from the group consisting of alkyl, cycloalkyl, aryl, alkenyl, cycloalkenyl and the said radicals hydroxy-substituted, halogen-substituted and amino-substituted, X is halogen, alkoxy of from 1 to 10 carbon atoms, aryloxy of from 1 to 20 carbon atoms, alkali metaloxy, alkaline earth metaloxy, carboxy or amino and (Si) is selected from the group consisting of $$-\mathrm{Si}\!\!\leqslant$$

and $$-\mathrm{Si(R)_2-O-Si}\!\!\leqslant,$$

and calcining the polymerized product, said silane being admixed with a second component, R'$_n$MY$_m$, wherein R' is the same as R, Y is selected from the group consisting of the same groups as X and oxygen, M is selected from the group consisting of iron, nickel, cobalt, platinum, palladium, aluminium and mixtures thereof, $m$ is any number greater than 0 and up to 8 and $n$ is from 0 to any number less than 8.

2. The process of claim 1 wherein X is chlorine.

3. The process of claim 2 wherein R(Si)X$_3$ is selected from the group consisting of phenyl trichlorosilane, (C$_6$H$_5$)$_3$Si—O—SiCl$_3$, methyl trichlorosilane, ethyl trichlorosilane, dodecyl trichlorosilane and mixtures thereof.

4. The process of claim 1 wherein the calcination step is carried out at a temperature of from about 200° C to about 600° C.

5. The process of claim 1 wherein M includes aluminum as an aluminum alkoxide of from 1 to 10 carbon atoms.

6. The process of claim 1 wherein M includes aluminum as aluminum chloride.

7. The process of claim 1 wherein there is present in the hydrolysis and polymerization steps an inorganic compound consisting of an anion of M and Y and a cation selected from the group consisting of hydrogen, alkali metal, alkaline earth metal and ammonium.

8. The process of claim 7 wherein the said compound is selected from the group consisting of sodium ethyl chloroplatinate, chloroplatinic acid and sodium aluminate.

9. The process of claim 1 wherein X is alkoxy.

10. The process of claim 9 wherein X is methoxy.

11. The process of claim 10 wherein the silane is selected from the group consisting of phenyl trimethoxysilane and ethylenediaminopropyl trimethoxysilane.

12. The process of claim 1 wherein the steps of hydrolyzing and polymerizing are carried out in the presence of water and an organic solvent.

13. The process of claim 12 wherein the organic solvent is an alcohol.

14. The process of claim 13 wherein the alcohol is methanol.

15. The process of claim 1 wherein the steps of hydrolyzing and polymerizing are carried out in the presence of water and a base.

16. The process of claim 15 wherein the base is selected from the group consisting of pyridine and triethylamine.

17. The process of claim 1 wherein M is a metal selected from the group consisting of iron, cobalt, nickel, palladium, platinum and mixtures thereof.

18. The process of claim 1 wherein said process conditions include a temperature of from about 300° to about 600° C, a pressure of from about 1 atmosphere to about 10 atmospheres, a gas hourly space velocity, expressed at standard temperature and pressure, of from about 6,000 hr$^{-1}$ to about 60,000 hr$^{-1}$ and a hydrogen/feedstock mole ratio of from about 2 to about 4.

* * * * *

UNITED STATES PATENT AND TRADEMARK OFFICE
CERTIFICATE OF CORRECTION

PATENT NO. : 4,086,261
DATED : April 25, 1978
INVENTOR(S) : THOMAS OWEN MITCHELL and
DARRELL DUAYNE WHITEHURST It is certified that error appears in the above-identified patent and that said Letters Patent are hereby corrected as shown below:

Column 1, line 8: After the expression "4,003,825" insert -- which was a division of application Serial No. 450,967, --.

Column 6, line 8: "0.1 hr.$^{-2}$" should be -- 0.1 hr.$^{-1}$ --.

Column 10, line 12: In formula "SI" should be -- Si --.

Column 10, line 43: In formula "Ch$_2$" should be -- CH$_2$ --.

Column 10, line 56: In formula "SI" should be -- Si --.

Signed and Sealed this

Fifth Day of December 1978

[SEAL]

Attest:

RUTH C. MASON
Attesting Officer

DONALD W. BANNER
Commissioner of Patents and Trademarks